United States Patent
Shennib

(10) Patent No.: US 7,313,245 B1
(45) Date of Patent: Dec. 25, 2007

(54) INTRACANAL CAP FOR CANAL HEARING DEVICES

(75) Inventor: Adnan Shennib, Danville, CA (US)

(73) Assignee: InSound Medical, Inc., Newark, CA (US)

( * ) Notice: Subject to any disclaimer, the term of this patent is extended or adjusted under 35 U.S.C. 154(b) by 1054 days.

(21) Appl. No.: 09/721,462

(22) Filed: Nov. 22, 2000

(51) Int. Cl.
*H04R 25/00* (2006.01)
*H04R 25/02* (2006.01)
*A61B 7/02* (2006.01)
*A61F 11/00* (2006.01)

(52) U.S. Cl. .............. 381/325; 381/328; 181/135; 181/130; 128/864

(58) Field of Classification Search .......... 381/325, 381/328; 181/135, 129, 130; 128/864, 867, 128/865; 180/130
See application file for complete search history.

(56) References Cited

U.S. PATENT DOCUMENTS

| | | | | |
|---|---|---|---|---|
| 4,344,425 A * | 8/1982 | Strauss | ............... | 128/864 |
| 4,553,627 A * | 11/1985 | Gastmeier et al. | .......... | 181/135 |
| 4,706,778 A * | 11/1987 | Topholm | .............. | 181/135 |
| 4,870,689 A * | 9/1989 | Weiss | .............. | 381/325 |
| 4,987,597 A * | 1/1991 | Haertl | .............. | 381/325 |
| 5,238,613 A * | 8/1993 | Anderson | .............. | 264/425 |
| 5,327,500 A * | 7/1994 | Campbell | .............. | 381/325 |
| 5,352,316 A * | 10/1994 | Steer | .............. | 156/252 |
| 5,401,920 A * | 3/1995 | Oliveira | .............. | 181/135 |
| 5,488,961 A * | 2/1996 | Adams | .............. | 128/864 |
| 5,573,015 A * | 11/1996 | Williams | .............. | 128/864 |
| 5,825,896 A * | 10/1998 | Leedom | .............. | 381/322 |
| 6,000,492 A * | 12/1999 | Puthuff et al. | .............. | 181/135 |
| 6,105,713 A * | 8/2000 | Brimhall et al. | .............. | 181/135 |
| 6,129,174 A * | 10/2000 | Brown et al. | .............. | 181/135 |
| 6,134,333 A * | 10/2000 | Flagler | .............. | 381/325 |
| 6,145,226 A * | 11/2000 | Finlayson | .............. | 40/310 |
| 6,164,409 A * | 12/2000 | Berger | .............. | 181/135 |
| 6,179,085 B1 * | 1/2001 | Brimhall et al. | .............. | 181/135 |
| 6,382,346 B2 * | 5/2002 | Brimhall et al. | .............. | 181/135 |

\* cited by examiner

*Primary Examiner*—Ping Lee
*Assistant Examiner*—Devona E. Faulk
(74) *Attorney, Agent, or Firm*—Townsend and Townsend and Crew LLP

(57) ABSTRACT

An acoustically permeative intracanal cap is adapted to be worn semi-permanently deep in the ear canal for shielding a hearing device positioned deeper within the ear canal against moisture and debris infiltration. The intracanal cap conforms circumferentially to the walls of the ear canal for occlusion thereof, and comprises a porous membrane with pores sized to prevent water and solid debris from entering the ear canal while allowing air-conducted sounds to freely reach the microphone of the shielded hearing device. The intracanal cap may be entirely separate from the hearing device for independent insertion and removal, or attached to a lateral section of the hearing device for concurrent insertion and removal therewith into and from the ear canal.

11 Claims, 6 Drawing Sheets

INTRACANAL CAP FOR CANAL HEARING DEVICES

CROSS-REFERENCE TO RELATED APPLICATIONS

This application is related to co-pending patent application Ser. No. 09/327,717, filed Aug. 2, 1999, titled "Extended Wear Canal Hearing Device" (the "'717 application"), and U.S. Pat. No. 6,137,889 titled "Direct Tympanic Membrane Excitation Via a Vibrationally Conductive Assembly" (the "'889"), each of which is assigned to the assignee of the present application.

BACKGROUND OF THE INVENTION

1. Technical Field

The present invention relates generally to miniature hearing aids, acoustic and otherwise, which are fitted deeply in the ear canal.

2. Description of the Prior Art (1) Brief Description of the Ear Canal and Canal Hearing Aids The external acoustic meatus (ear canal) is generally narrow and contoured as shown in the coronal view in FIG. 1. The ear canal 10 is an elongated cavity beginning at the canal aperture 17 and ending medially with the tympanic membrane 18 (eardrum). The cartilaginous region 11 is relatively flexible due to the underlying cartilaginous tissue. The medial (towards the tympanic membrane) part, a bony region 13 proximal to the tympanic membrane, is rigid due to the underlying bony tissue. The skin 14 in the bony region 13 is thin (relative to the skin 16 in the cartilaginous region) and is more sensitive to touch or pressure. There is a characteristic bend 15 that roughly occurs at the bony-cartilaginous junction 19 (referred to herein as the bony junction), which separates the cartilaginous 11 and the bony 13 regions. The magnitude of this bend varies among individuals. The cross section of the ear canal is generally oval (FIG. 2) having a long diameter ($D_L$) and a short diameter ($D_S$)

Hair 12 and debris 4 in the ear canal are primarily present in the cartilaginous region 11. Physiologic debris includes cerumen (earwax), sweat, exfoliated skin and hair, and oils produced by the various glands underneath the skin in the cartilaginous region. Non-physiologic debris consists primarily of environmental particles that enter the ear canal. Canal debris is naturally extruded to the outside of the ear by the process of lateral epithelial cell migration that begins on the eardrum and extends the length of the ear canal. There is no cerumen production or hair in the bony part of the ear canal. Laterally and external to the ear canal is the concha cavity 2 and the auricle 3, both also cartilaginous.

Conventional canal hearing aids are removed daily from the ear in order for the ear canal to "dry out" after being occluded by the hearing aid.

(2) Review of State-of-the-Art in Canal Hearing Aid Technology

Recent advances have led to the development of extended-wear canal hearing devices, which are operated continuously deep in the ear canal for several months before removal. These deep canal hearing devices are completely inconspicuous, thus very desirable for the hearing impaired who may be concerned with the social stigma and vanity associated with wearing a visible hearing aid. For example, in the aforementioned related '717 application, Shennib et al. describe an extended wear canal hearing device primarily positioned in the bony part of the ear canal. The canal device in the '717 application is of the air-conduction type since it relies on air-conducted sounds emitted by a receiver (speaker) to excite the eardrum. Similar to other air conduction hearing aids, acoustic sealing is required for the prevention of acoustic feedback.

In the other aforementioned '889 patent, the hearing device is similarly positioned inconspicuously in the bony part of the ear canal. However, the excitation of the eardrum occurs via a vibrational filament which makes direct contact thereto.

These and other hearing devices of the prior art rely on water-proofing elements integrated within for protection. For example, moisture guards are incorporated onto the microphone and the receiver for protecting the transducer from the damaging effects of moisture, cerumen and water-borne debris. The coating or enclosure of the body of the device must also be water proof since water exposure (e.g., during showering, or swimming) is expected for extended-wear devices that are worn continuously in the ear canal.

However, even with water proofing means incorporated onto the device, water and water-born debris is likely to accumulate on the body of the hearing device during its long term wear causing the device to ultimately malfunction. Furthermore, water contaminants in the ear canal may accumulate around the hearing device enhancing microbial growth which leads to irritation and infections in the ear canal.

Review of Protective Ear Covers

Ear canal protection for applications other than hearing device wear is well known. For example, Jordan-Ross in U.S. Pat. No. 4,916,758 discloses an ear protector for beautician use during applications of liquid treatments which may affect the ear canal. Adams in U.S. Pat. No. 5,488,961 discloses an ear plug that is hydrophobic for allowing hearing while preventing water from entering the ear canal during swimming and other water activities. The earplug is elongated with a lumen extending along the ear canal. These and other related inventions may interfere with a hearing device worn in the ear canal and inadvertently even damage the device or injure the device wearer, because they are merely intended to protect the ear canal.

A key goal of the present invention is to provide a hydrophobic barrier for the protection of a deep canal hearing device during its extended wear in the ear canal.

Another goal of the present invention is to protect the ear canal from water and water-borne contaminants during wear of a canal hearing device.

SUMMARY OF THE INVENTION

The invention provides an acoustically permeative cap worn semi-permanently in the ear canal for protecting a hearing device positioned deeper within the canal. The intracanal cap conforms circumferentially to the walls of the ear canal to occlude the canal at the locations of the cap. It comprises a porous membrane with pores sized to prevent water (fluids) and solid debris from entering the ear canal, and thus provides a barrier or shield against these liquid and solid contaminants from infiltrating the canal and reaching the hearing device, while allowing passage of air-conducted sounds to freely reach the microphone of the hearing device medially positioned within the canal. The protection provided by the intracanal cap thus improves reliability and longevity of the hearing device, and reduces the need heretofore required for a durable enclosure, resulting in lower cost of manufacturing for the hearing device.

In the preferred embodiment, the intracanal cap is configured separately from the hearing device. Thus, the cap can be independently inserted and removed. Alternatively, the cap may be configured attached laterally to the hearing device for positioning in the ear canal simultaneously therewith. The intracanal cap comprises a flexible ring which fits in a sealing and retaining manner along the interior walls of the ear canal. The central porous membrane is hydrophobic, to repel water coming from the outside. The canal hearing device, protected by the intracanal shield, may be of any type including acoustic output types (with a speaker), a direct tympanic drive type (with a vibrator touching the eardrum), or an electromagnetic type (with a magnet on the eardrum). The intracanal shield is preferably inserted in the deeper portion of the ear canal past the region of hair and cerumen production. For safety reasons, the insertion may be performed by a health car professional such as an otolaryngologist or an audiologist. The intracanal cap is particularly applicable for extended wear hearing devices.

BRIEF DESCRIPTION OF THE DRAWINGS

The above and still further goals, objectives, features, aspects and attendant advantages of the present invention will be better understood from the following detailed description of the best mode presently contemplated for practicing the invention, with reference to preferred embodiments and methods, and the accompanying Figures of drawing, in which.

DETAILED DESCRIPTION OF THE PREFERRED EMBODIMENTS AND METHODS

Figure 1:
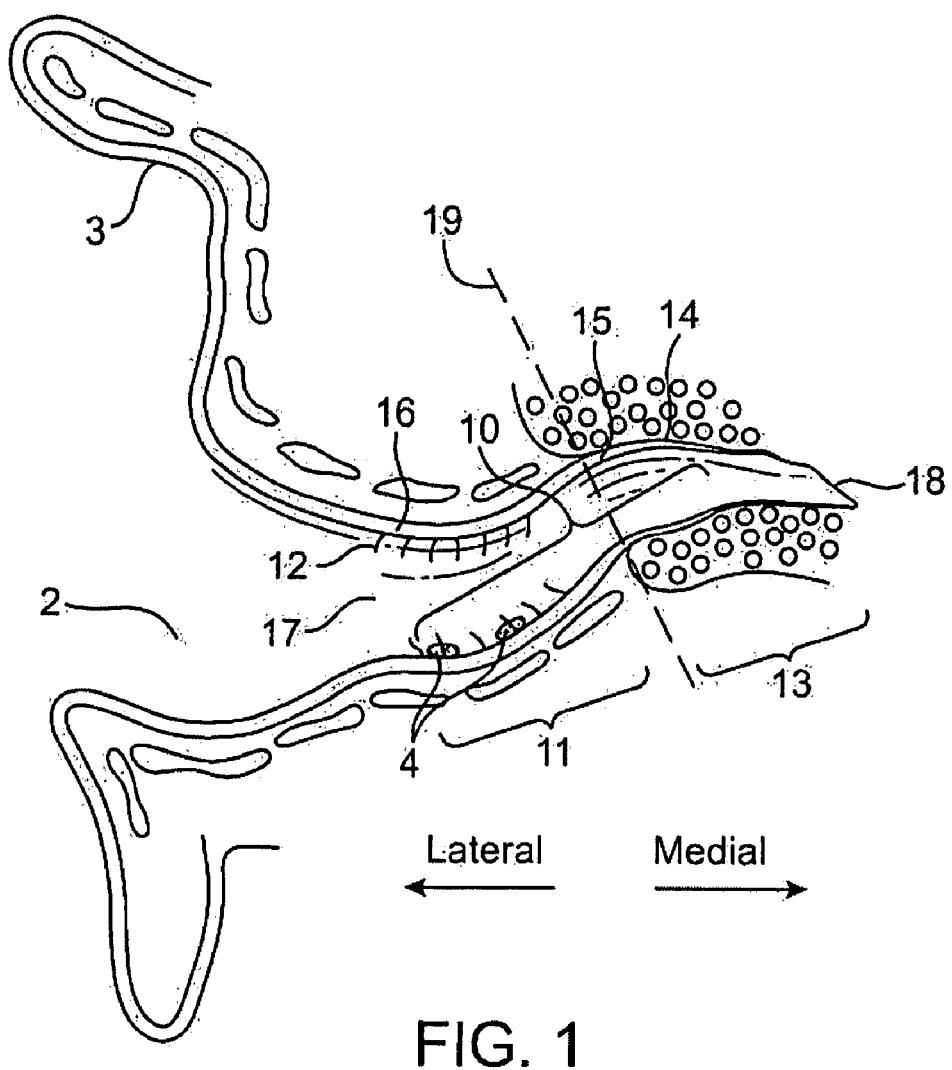
FIG. 1 is a side view (top) of the external ear illustrating the tortuously elongated ear canal, as described above.
Figure 2:
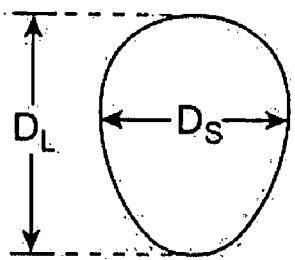
FIG. 2 is a cross sectional view of the ear canal in FIG. 1 showing its oval cross section.

The present invention, illustrated in FIGS. 3-10, provides an intracanal cap 20 which occludes the ear canal 10 and protects a canal hearing device 40 placed deep in the ear canal in proximity to the eardrum 18. The intracanal cap 20 comprises a retention ring 21 and a porous shield 22. The retention ring 21 conforms to the walls of the ear canal 10 when inserted within. The porous shield 22 comprises pores sized to allow incoming air-conducted sounds 50 to pass through (arrow 52) towards the hearing device 40 and remaining medial portion of ear canal. But the pore sizes are also designed or selected to prevent fluids and solid debris from reaching the hearing device 40 and causing damage thereto. The hearing device 40 typically comprises a microphone 41 with microphone port 42, a receiver (speaker) 43 with receiver port 44, battery 45, electronic components 46 and other parts not shown for clarity. A sealing retainer 47 holds the hearing device 40 in place and seals the ear canal for preventing acoustic feedback.

Figure 4:
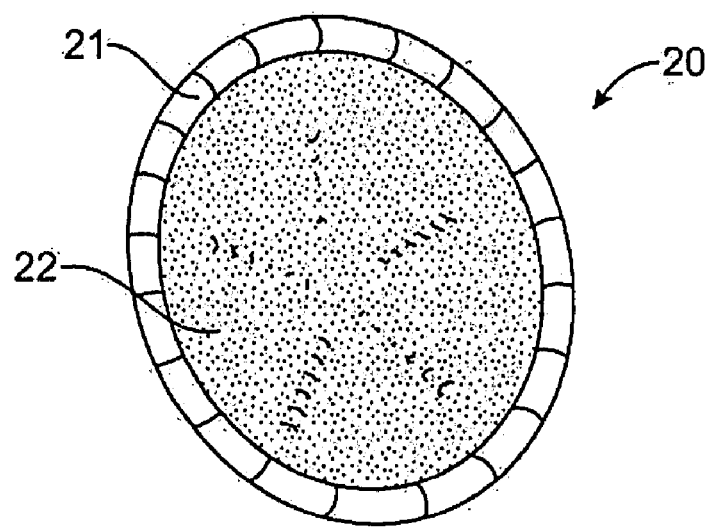
FIG. 4 is a front view of an embodiment of the invented cap showing a flexible ring and acoustically transparent, relatively flat porous membrane.

Incoming sounds 50 pass through the porous shield 22 of the intracanal cap 20 which may be made in various embodiments as shown in FIGS. 4-7. FIG. 4 shows a diaphragm embodiment having flexible ring 21 and a relatively flat central membrane 22. The ring is flexible to conform to the shape and size of the ear canal. An elastomeric biocompatible material such as silicone is preferably used for the ring. The ring is adhered to the porous shield via the appropriate adhesive. The thickness and pore size of the porous shield must be selected to optimize the acoustic transmission without adversely affecting the water breakthrough rating. It is understood that a thinner membrane and larger pore sizes would have better transmission of sound but with lower rating for water breakthrough. Conversely, thicker membrane and smaller pore sizes will improve the water breakthrough rating at the expense of sound transmission. Porous shields with pore sizes in the range of 1 to 10 microns and thickness in the range of 50 to 250 microns were found to be optimal for good sound transmission. The specific combination of pore size and thickness is selected depending on the water breakthrough rating desired.

Various hydrophobic porous shield materials were tested and found to offer good results in terms of acoustic transparency (i.e., permeability) and thickness. These materials include Poseidon™ (manufactured by PALL Specialty Materials). Certain hydrophobic membranes are also oleophobic which aid in repelling earwax produced in the ear canal away from the hearing device. These membranes include ZITEX™ (manufactured by W. L. Gore & Associates, Inc.), Versapor® R and Supor® R (both manufactured by PALL Specialty Materials). These materials are typically made of acrylic copolymers, polyethersulfone polymer, and fluorpolymer. These and other materials are typically treated and supported by other materials for enhanced structure, hydrophobicity and oleophobicity.

Figure 5:
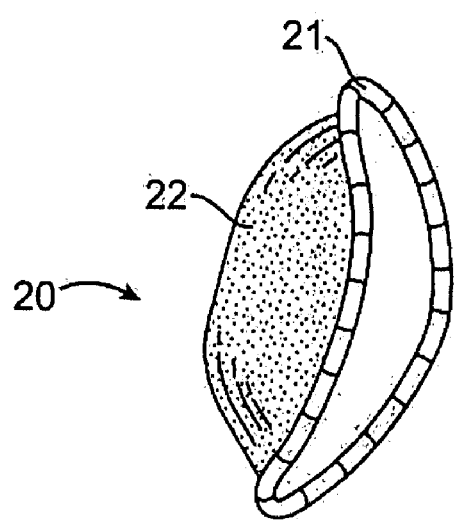
FIG. 5 is an alternate embodiment of the invented cap having a bulged porous membrane.
Figure 6:
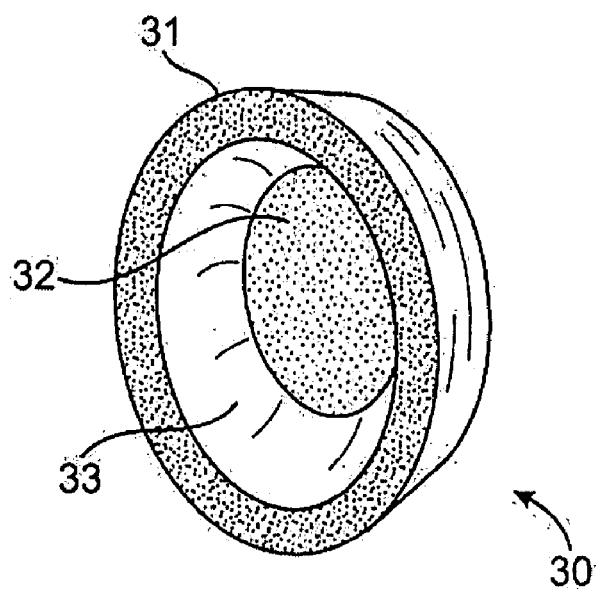
FIG. 6 is a perspective view of an embodiment of the invented intracanal cap made of polyurethane foam.
Figure 7:
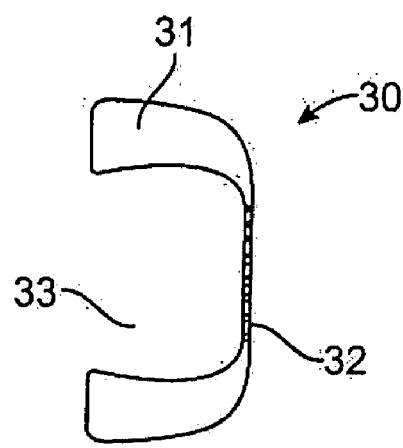
FIG. 7 is a side view of the embodiment of FIG. 6.

FIG. 5 shows an embodiment of the intracanal cap having a bulging porous shield 22. FIGS. 6 and 7 show an embodiment made of polyurethane foam which is inherently porous and particularly air conductive when formed thinly. The foam cap 30 is formed with a hollow cylindrical ring 31 on the perimeter and having thin porous membrane 32 at its center. The advantage of the foam cap is that it is fabricated from a single material during the manufacturing process. The intracanal cap may also be made entirely from other polymeric materials such as silicone having small perforations at its center. The perforations may be treated with hydrophobic material to enhance hydrophobicity.

The intracanal caps shown in FIGS. 3-7 are configured separate from the canal hearing device. Thus, each cap can be inserted into and removed from the ear canal independently from the hearing device. The intracanal cap is preferably made oval in cross sectional shape, as shown in FIG. 6, and sufficiently flexible to assume the oval or irregular shape of the ear canal.

Figure 8:
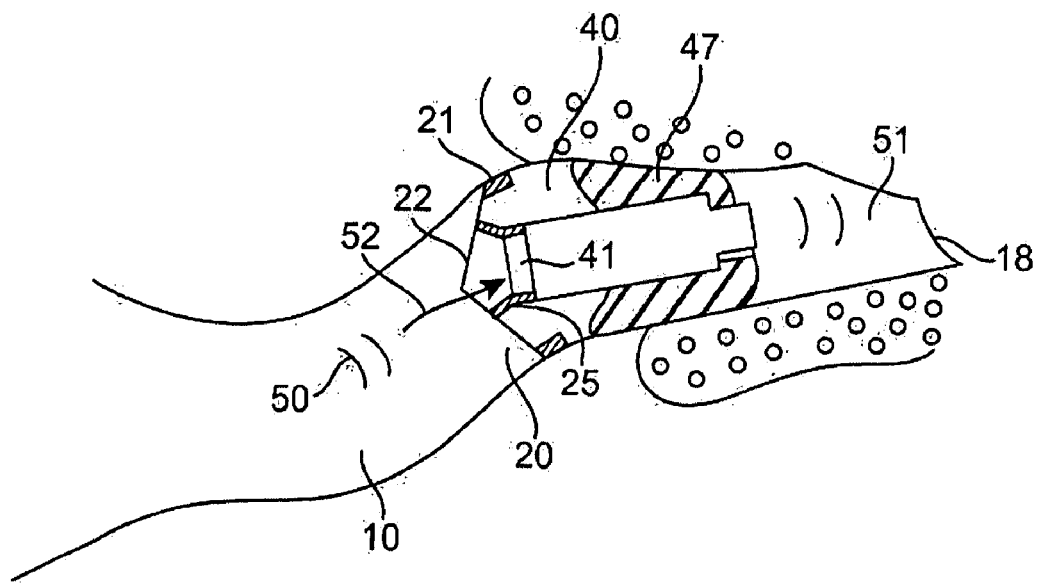
FIG. 8 is a view of an alternate embodiment of the canal cap attached to a lateral section of an acoustic canal hearing device used for extended wear.

FIG. 8 shows an alternate embodiment of the invented intracanal cap 20 connected to a canal hearing device 40. Similar to the separate cap embodiment, the intracanal cap of this embodiment comprises a retention ring 21 and a porous membrane 22 for allowing incoming sounds 50 to reach the microphone 41 of the hearing device. The attached intracanal cap allows the cap to be inserted and removed along with the hearing device 40.

Figure 3:
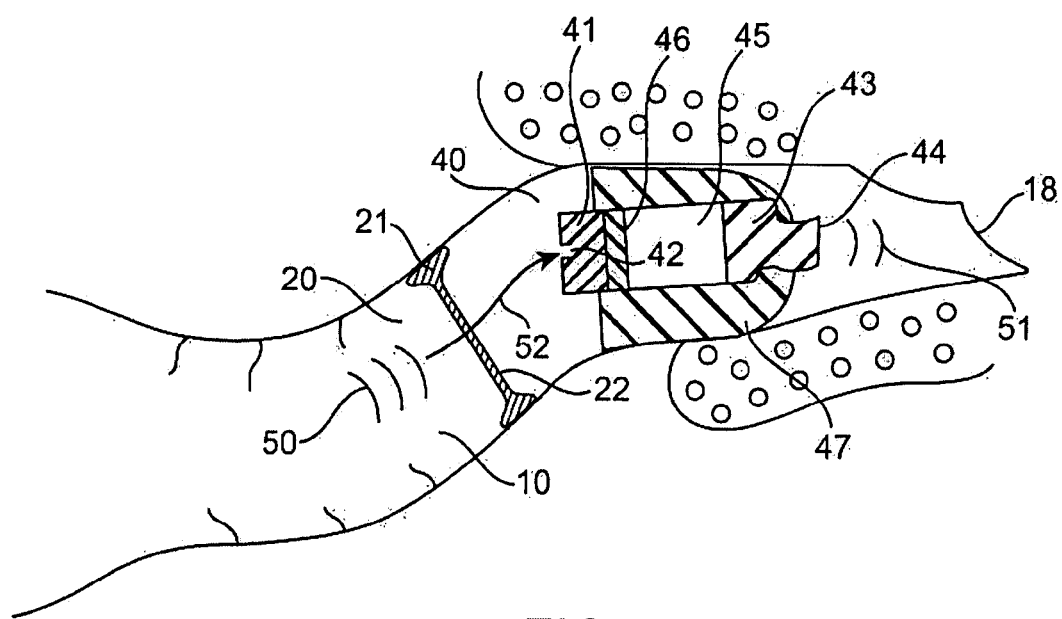
FIG. 3 is a side view of a preferred embodiment of the invented canal cap which is acoustically transparent and hydrophobic for protecting a canal device medially positioned from water and debris.
Figure 9:
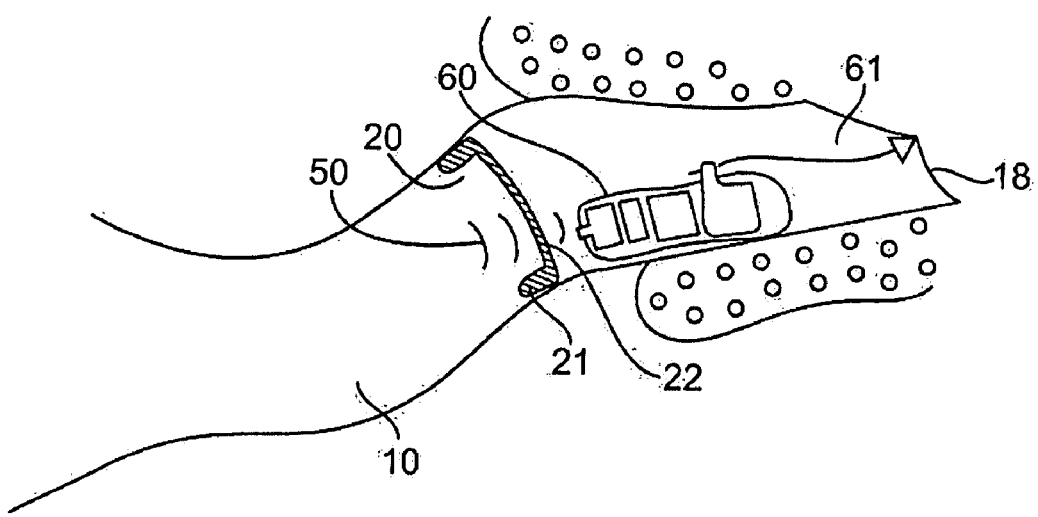
FIG. 9 is a view of the invented intracanal cap used in conjunction with a direct tympanic drive hearing device.
Figure 10:
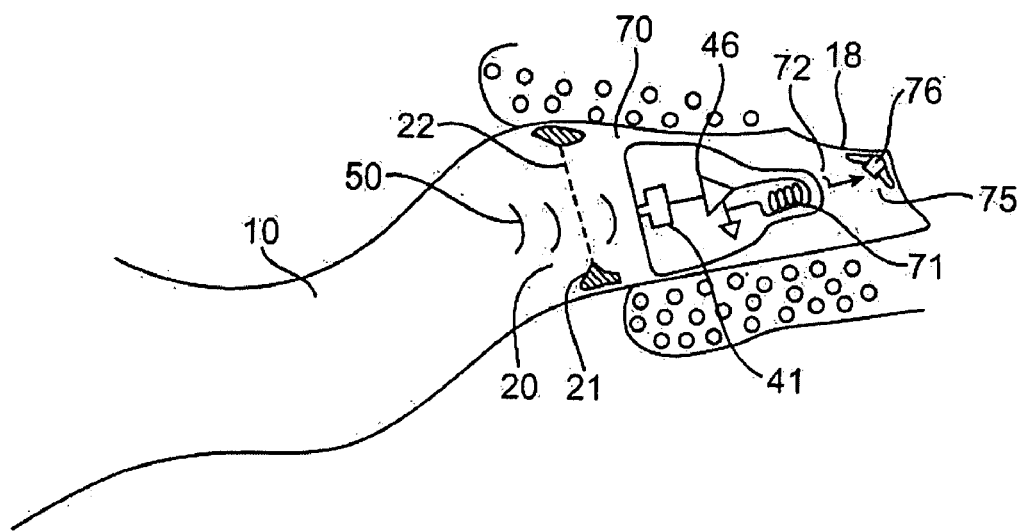
FIG. 10 is a view of the invented intracanal cap used in conjunction with an electromagnetic hearing aid having a magnet on the eardrum.

The invented intracanal cap may be used with canal hearing devices having acoustic output (speaker) as shown in FIGS. 3 and 8. The intracanal cap protects the hearing device and particularly its transducer mechanisms subject to damage from water and contaminants. The intracanal cap of the present invention is equally suited for hearing devices comprising alternate configurations in the ear canal. In FIG. 9 for example, the intracanal cap 20 is used to protect a non-occluding hearing device 60 of the type described in the aforementioned '889 patent. In this hearing device configuration, a vibrating filament assembly 61 directly excites the eardrum 18. FIG. 10 shows yet another canal device configuration having a tympanic contact transducer of the type described in U.S. Pat. No. 5,259,032. In this configuration, the hearing device 70 comprises an electromagnet coil 71 which vibrates a tympanic transducer 75 attached to the eardrum 18. The tympanic transducer comprises a magnet 76 which responds to magnetic fields 72 produced by the coil 71. The magnetic field 72 is representative of incoming acoustic signals 50.

The intracanal cap of the present invention is not limited to the canal hearing device configurations shown in FIGS. 3 and 8-10, but may be used with any hearing device placed deeply in the ear canal. Regardless of the configuration, the intracanal cap protects the worn hearing device, and thus improves its reliability and longevity. This protection also reduces the requirement for a protective enclosure resulting in lower cost of manufacturing for the hearing device.

The intracanal shield and the associated hearing device are preferably disposable, to be discarded once removed from the ear canal. The capping shield is preferably inserted in the deeper portion of the ear canal past the region of hair and cerumen production. For safety reasons, the insertion is preferably made by a health care professional such as an otolaryngologist or an audiologist if the shield is to be inserted too deeply in the ear canal.

The intracanal cap is particularly suitable for use with extended wear hearing devices, in which the device operates in the ear canal continuously for several months, thus requiring protection from water and contaminants. The intracanal cap also protects the ear canal itself from water and infectious contaminants by preventing the entry of debris and contaminants into the ear canal. This debris can otherwise accumulate on and around the hearing device leading to bacterial and fungal growth in the ear canal. Furthermore, the porosity of the membrane allows for healthy air circulation in the ear canal, and in certain non-occuluding device embodiments, up to the eardrum. This air circulation minimizes bacterial and fungal growth, which occurs in enclosed humid environments.

Although a presently contemplated best mode of practicing the invention has been disclosed herein by reference to certain preferred embodiments and methods, it will be apparent to those skilled in the art that variations and modifications of the disclosed embodiments and methods may be implemented without departing from the spirit and scope of the invention. It is therefore intended that the invention shall be limited only to the extent required by the appended claims and the rules and principles of the applicable law.

What is claimed is:

1. An intracanal shield for positioning entirely in the ear canal and capping the cavity of said ear canal, comprising:
   a retention ring adapted to conform to the wall of the ear canal cavity,
   a central porous member disposed within the retention ring having pores sized for allowing air to pass through said porous member to provide a circulated air flow in the ear canal while preventing passage of fluids and solids therethrough,
   wherein said intracanal shield, when fitted in said retaining manner in the ear canal cavity and positioned laterally with respect to a miniature hearing device medically positioned in close proximity to the eardrum, protects said hearing device against penetration of fluids and debris through said porous member while allowing air-borne sounds to reach said hearing device, wherein said intracanal shield is separate from said canal hearing device for independent insertion and removal while said hearing device is positioned in-situ.

2. The intracanal shield of claim 1, wherein said central porous member is hydrophobic.

3. The intracanal shield of claim 1, wherein said porous member is oleophobic.

4. The intracanal shield of claim 1, wherein said porous member comprises a porous membrane.

5. The intracanal shield of claim 1, wherein said intracanal shield is composed of disposable material for cost-effective single use of said shield.

6. The intracanal shield of claim 1, wherein said shield is at least partially composed of polyurethane form.

7. The intracanal shield of claim 1, wherein said shield is at least partially composed of a silicone material.

8. The intracanal shield of claim 1, wherein said pores are sized in the rage of 1 to 10 microns.

9. The intracanal shield of claim 1, wherein the retention ring of said intracanal shield is shaped and dimensioned to be positioned deep in the ear canal past the hair and ceriman production area therein.

10. The intracanal shield of claim 1, wherein said intracanal shield has an oval cross sectional shape adapted to fit comfortably in a cross section of the ear canal.

11. A hearing system fabricated and adapted to be positioned entirely in the ear canal for extended wear, said system comprising:
    a hearing device assembled and dimensioned to be medially positioned in the ear canal; and
    the intracanal shield of any one of claims 1 to 10.

* * * * *